United States Patent [19]
Koshiyama et al.

[11] 4,451,456
[45] * May 29, 1984

[54] ANTITUMOR ANTIBACTERIAL AGENTS

[75] Inventors: Hideo Koshiyama, Musashino; Fumihide Sakai, Yokohama; Hiroaki Ohkuma, Tokyo, all of Japan

[73] Assignee: Bristol-Myers Company, New York, N.Y.

[*] Notice: The portion of the term of this patent subsequent to Nov. 23, 1999 has been disclaimed.

[21] Appl. No.: 390,149

[22] Filed: Jun. 21, 1982

Related U.S. Application Data

[60] Division of Ser. No. 122,626, Mar. 6, 1980, Pat. No. 4,360,458, which is a continuation-in-part of Ser. No. 026,488, Apr. 2, 1979, abandoned.

[51] Int. Cl.$^3$ .................... A61K 37/00; C07C 103/52; C07G 7/00
[52] U.S. Cl. ............................ 424/177; 260/112.5 R; 260/112 R
[58] Field of Search .................... 260/112.5 R, 112 R; 424/177

[56] References Cited
U.S. PATENT DOCUMENTS
4,360,458 11/1982 Koshiyama et al. ......... 260/112.5 R Primary Examiner—Delbert R. Phillips
Attorney, Agent, or Firm—Robert E. Carnahan

[57] ABSTRACT

An antitumor antibacterial complex referred to as BBM-928 is described which is produced by microbiological fermentation under controlled conditions using a species of actinomycetes. The bioactive components of the complex have pronounced antitumor activity and are moderately to weakly active against gram-positive and acid fast bacteria but practically inactive against gram-negative bacteria and fungi. Based on median survival time, the component designated BBM-928A is substantially more active than mitomycin C by a factor of 10 to 300 fold against intraperitoneally implanted mouse tumors.

4 Claims, 8 Drawing Figures

FIG. 1
INFRARED SPECTRUM OF BBM-928 A

FIG. 2
INFRARED SPECTRUM OF BBM-928 B

FIG. 3
INFRARED SPECTRUM OF BBM-928 C

FIG. 4
INFRARED SPECTRUM OF BBM-928 D

FIG. 5
NMR SPECTRUM OF BBM-928 A

FIG. 6
NMR SPECTRUM OF BBM-928 B

FIG. 7
NMR SPECTRUM OF BBM-928 C

FIG. 8
NMR SPECTRUM OF BBM-928 D

ANTITUMOR ANTIBACTERIAL AGENTS

CROSS-REFERENCE TO RELATED APPLICATION

This application is a division of our copending application Ser. No. 122,626 filed Mar. 6, 1980 and now U.S. Pat. No. 4,360,458 patented Nov. 23, 1982 which in turn is a continuation-in-part of U.S. application Ser. No. 026,488, filed Apr. 2, 1979 and now abandoned.

BACKGROUND OF THE INVENTION

This invention is concerned with a new antitumor antibiotic complex and processes for production, recovery and separation into bioactive components.

Based on present spectral data and available physicochemical properties, the antitumor antibiotic complex of the present invention appears to be structurally related to the quinoxaline group of antibiotics such as echinomycin, Dell, et al., J. Am. Chem. Soc., 97, 2497 (1975), quinomycins, Shoji, et al., J. Antibiotics, 14A, 335 (1961), and triostin C, The Merck Index, 9th Ed., 9399. However, the antitumor antibiotic complex is differentiated from these antibiotics in the following aspects:

1. The instant complex and components thereof contain a quinoline nucleus as a chromophore instead of quinoxaline as in the actinoleukin group of antibiotics.
2. The instant complex and components thereof do not contain sulfur in contrast to the presence of disulfide or thioacetal bridge in the structure of actinoleukin antibiotics.
3. The instant complex and components thereof show relatively weak antimicrobial activity compared to the actinoleukins which are potent antibacterial antibiotics.

SUMMARY OF THE INVENTION

A new antitumor antibiotic complex designated BBM-928 is provided by the present invention. The complex, which contains at least six components, is prepared by cultivating a BBM-928 producing strain of actinomycetes (ATCC 31491) or a mutant thereof in an aqueous nutrient medium employing submerged aerobic conditions. This invention also deals with a process for recovering the BBM-928 complex from the culture medium and separation of the complex into its bioactive components by countercurrent distribution and chromatographic techniques.

The scope of this invention comprehends the BBM-928 complex and bioactive components BBM-928 A, B, C, D, E, and F thereof. It is particularly concerned with components BBM-928 A, B, C, and D in dilute forms, as true concentrates and in purified form.

DETAILED DESCRIPTION OF THE INVENTION

This invention is concerned with a new antitumor antibiotic complex arbitrarily designated herein as BBM-928. The complex is believed to be structurally related to the actinoleukin group of antibiotics and is formed by fermentation of as yet unidentified strain of actinomycetes. Any strain of actinomycetes capable of forming BBM-928 in culture medium may be used with the preferred producing microorganism designated actinomyctes species strain No. G455-101 in the Bristol-Banyu culture collection. The microorganism was isolated from a soil sample collected in the Philippine Islands and has been deposited with the American type culture collection of microorganisms as ATCC 31491.

The novel antitumor antibiotic complex of the instant invention referred to herein has at least six components designated BBM-928A, B, C, D, E and F. Components A, B, C and D of the BBM-928 complex have been isolated in crystalline form with chemical structures of components A, B and C identified. The complex (and individual components) of this invention have antitumor antibacterial properties. With respect to antibacterial activity, the complex and individual components thereof are useful as nutritional supplements in animal feeds and as therapeutic agents in treating bacterial infection in mammals. Additionally, the antibiotics are useful in cleaning and sterilizing laboratory glassware and surgical instruments and may be used in combination with soaps, detergents and wash solutions for sanitation purposes. Regarding antitumor effects, the complex and individual components thereof are particularly useful against a variety of intraperitoneally implanted mouse tumors.

ACTINOMYCETES SPECIES STRAIN NO. G455-101

The following is a general description of the preferred microorganism producing the antibiotic antitumor complex BBM-928. Observations were made of the cultural, physiological, and morphological features of the organism in accordance with standard taxanomic methods, e.g., Shirling, et al., Int. J. Syst. Bacteriol. 16, 313 (1966) and Lechevalier, et al., Biol. Actinomycetes Related Org. 11, 78 (1976).

Micromorphology: Strain No. G455-101 forms both substrate and aerial mycelia, and the substrate mycelium is well-developed, long and branched (0.5–0.8μ in width). Distinct fragmentation of the substrate mycelium is not seen. Unlike ordinary species of *streptomyces*, strain G455-101 bears only short or rudimental aerial mycelia, or does not form any in some agar media. Short or long spore-chains are produced in the aerial mycelium, which contain 2-50 oval spores in a chain (mostly 5-20 spores). Spore-chains are straight, flexuous or looped in shape. The spores are spherical (0.3-0.4μ), oval or cylindrical (0.3×1.5-3.0μ) in shape and have smooth surface. Spores are often separated by empty hyphae. An amorphous sporangium-like vesicle which envelops short coiled spore-chain is observed occasionally on the aerial mycelium.

Cell Wall Composition and Whole Cell Sugar Components: The cell wall of strain G455-101 contains meso-diaminopimelic acid but lacks glycine. Whole cell hydrolyzate shows the presence of glucose, mannose and madurose (3-O-methyl-D-galactose). The aforementioned cell wall composition and whole cell sugar components indicate that strain G455-101 is an actinomycetes species of cell wall type IIIB.

Cultural and Physiological Characteristics: Strain G455-101 grows abundantly, forms pink or greyish pink aerial mycelium, and produces a reddish water-insoluble pigment in the nutritionally rich agar media, such as yeast extract-malt extract agar and oat meal agar. However, in inorganic salts-starch agar, glycerol-asparagine agar and tyrosine agar, it gives poor growth, forms white or beige rudimental aerial mycelium, and produces small amount of reddish pigment. Melanoid pigment is not produced in peptone-yeast-iron agar and tyrosine agar. Nitrate is reduced to nitrate. It grows abundantly at 28° C., 37° C., and 45° C., but does not grow at 10° C. or at 50° C. Pentoses and hexoses are well utilized by the strain. Cultural and physiological characteristics of strain G455-101 are shown in Tables 1 and 2, respectively. Utilization of carbon sources is shown in Table 3.

TABLE 1

Cultural Charateristics of Strain No. G455-101*

| | | |
|---|---|---|
| 1. Czapek's agar (Sucrose - nitrate agar) | G** | no or scant growth |
| | R | dark rose |
| | A | white to pale pink |
| | D | none |
| 2. Tryptone - yeast extract broth (ISP No. 1) | | moderate growth, floccose, sedimented and not pigmented |
| 3. Yeast extract - malt extract agar (ISP No. 2) | G | abundant |
| | R | deep red to reddish brown |
| | A | abundant, greyish pink to purplish pink |
| | D | none |
| 4. Oat meal agar (ISP No. 3) | G | abundant |
| | R | strong yellowish red |
| | A | moderate, pink |
| | D | greyish yellow |
| 5. Inorganic salts - starch agar (ISP No. 4) | G | poor |
| | R | light yellowish brown to dark red |
| | A | scant, white to beige |
| | D | none |
| 6. Glycerol - asparagine agar (ISP No. 5) | G | poor |
| | R | yellowish pink to reddish brown |
| | A | scant, white |
| | D | none |
| 7. Peptone-yeast extract-iron agar (ISP No. 6) | G | poor, plicate |
| | R | strong reddish orange |
| | A | none |
| | D | light yellowish orange |
| 8. Tyrosine agar (ISP No. 7) | G | poor |
| | R | dark red |
| | A | scant, white |
| | D | none |
| 9. Glucose-ammonium salts agar | G | poor |
| | R | reddish brown |
| | A | scant, light grey |
| | D | none |
| 10. Bennett's agar | G | moderate |
| | R | reddish brown |
| | A | restricted, greyish pink |
| | D | none |

*observed after incubation at 37° C. for 3 weeks.
**Abbreviation:
G — Growth
R — Reverse color of substrate mycelium
A — Aerial mycelium
D — Diffusible pigment

TABLE 2

Physiological Characteristics of Strain No. G455-101

| Test | Response | Method and medium |
|---|---|---|
| Nitrite from nitrate | Positive | Inorganic medium: Czapek's sucrose nitrate broth |
| Nitrite from nitrate | Positive | Organic medium: 0.5% yeast extract, 1.0% glucose, 0.5% KNO3, 0.1% CaCO3 |
| Casein hydrolysis in agar medium | Weakly positive | Luedemann's agar medium |
| Skimmed milk coagulation | Positive | |
| Gelatin liquefaction | Negative | 15% gelatin in tryptone-yeast extract broth (ISP No. 1 medium) |
| H2S production from L2-cysteine | Positive | L-Cysteine (0.1%) added to tryptone-yeast extract broth (ISP No. 1 medium) plus agar. H2S detected with a paper strip containing 10% aq. lead-acetate solution. |
| Formation of melanoid | Negative | Peptone-yeast-iron agar (ISP No. 6) and tyrosine agar (ISP No. 7). |
| Catalase reaction | Positive | H2O2 aq. solution |
| Oxidase reaction | Positive | Kovacs' reagent |
| Growth temperature | Abundant growth at 28, 37, and 45° C. Poor growth at 20° C. No growth at 10° C. and 50° C. | Bennett's agar |

TABLE 3

Utilization of Carbon Sources for Strain No. G455-101

| | PG | Lm |
|---|---|---|
| 1. Glycerol | ++ | + |
| 2. D(−)-Arabinose | + | + |
| 3. L(+)-Arabinose | + | + |
| 4. D-Xylose | ++ | + |
| 5. D-Ribose | ++ | + |
| 6. L-Rhamnose | ++ | + |
| 7. D-Glucose | + | + |
| 8. D-Galactose | ++ | + |
| 9. D-Fructose | ++ | + |
| 10. D-mannose | ++ | + |
| 11. L(−)-Sorbose | − | − |
| 12. Sucrose | − | − |
| 13. Lactose | −,± | − |
| 14. Cellobiose | + | + |
| 15. Meliboise | −,± | − |
| 16. Trehalose | + | + |
| 17. Raffinose | − | − |
| 18. D(+)-Melezitose | − | − |
| 19. Soluble starch | + | − |
| 20. Dulcitol | − | − |
| 21. Inositol | + | − |
| 22. D-Mannitol | ++ | + |
| 23. D-Sorbitol | − | − |
| 24. Salicin | − | − |
| 25. Cellulose | + | + |
| 26. Chitin | + | + |
| 27. Keratin | + | + |

Basal medium PG: Pridham - Gottlieb's inorganic medium, supplemented with 0.1% yeast extract
Lm: Luedemann's organic medium
Incubation for 2 weeks at 37° C.

It is to be understood that production of the BBM-928 complex of the present invention is not limited to the particular actinomycetes species strain No. G455-101 described by the above growth and microscopic characteristics. These characteristics are given for illustrative purposes only and the invention contemplates use of strains or mutants produced from the above-described organism by conventional means known to the art such as exposure to X-ray radiation, ultraviolet radiation, nitrogen mustard, phage exposure, and the like, which are capable of producing the BBM-928 complex or individual components thereof.

PREPARATION OF ANTITUMOR ANTIBIOTIC BBM-928 COMPLEX

The process of the present invention for producing the antitumor antibiotic BBM-928 complex comprises cultivating by fermentation actinomycetes strain No. G455-101 in an aqueous solution containing an assimilable carbon source and an assimilable nitrogen source under submerged aerobic conditions until substantial antitumor antibiotic activity is imparted to said solution. Conventional fermentation methods are employed in cultivating actinomycetes strain No. G455-101. Media which are useful for the production of the antibiotic antitumor agents of the instant invention include an assimilable source of carbon such as starch, glucose, dextrin, maltose, lactose, sucrose, fructose, mannose, molasses, glycerol and the like. The nutrient medium should also contain an assimilable nitrogen source such as protein, protein hydrolysate, polypeptides, amino acids, corn steep liquor, casein, urea and the like as well as nutrient inorganic salts which provide inorganic anions and cations such as potassium, sodium, ammonium, calcium, sulfate, carbonate, phosphate, chloride, nitrate, and the like.

In producing the BBM-928 complex, any temperature conducive to satisfactory growth of the organism may be employed. Temperatures ranging from about 20° to 45° C. are operable with a preferred temperature for optimizing growth of the organism ranging from about 28° to 34° C. with a temperature range of 30° to 32° most preferred. Maximum production of the BBM-928 complex is generally obtained in about 4 to 6 days. Conventional methods are employed in the fermentation period. For example, preparation of small amounts is conveniently carried out in shake flasks or by surface cultures. Preparation of large amounts is preferably carried out under submerged aerobic culture conditions in sterile tanks. With tank fermentation a vegetative inoculum is first produced in a nutrient broth by innoculating the broth culture with a spore from the organism to provide a young active seed culture which is then aseptically transferred to the fermentation tank medium. Aeration in tanks and bottles may be provided by forcing sterile air through or onto the service of the fermenting medium with further agitation in tanks provided by a mechanical impeller. Anti-foaming agents such as silicone oil, soybean oil and lard oil may be added as needed.

Antibiotic levels in the fermentation broth or the extracts of BBM-928 complex can be determined by paper disc agar-diffusion assay using *Sarcina lutea* as a test organism and employing nutrient agar as the assay medium. The pH is adjusted 9.0 for optimal sensitivity of the assay system which is used to determine optimum broth potency.

The BBM-928 complex is isolated from the fermentation broth by conventional means such as solvent extraction procedures. Purification is conveniently carried out by preparative countercurrent distribution and chromatographic procedures as more fully described in Examples 2 and 3 below to provide BBM-928 components A, B, C, D, E, and F.

PHYSICO-CHEMICAL PROPERTIES OF BBM-928 COMPONENTS A, B, C, and D OF EXAMPLE 3

Individual components of BBM-928 show solubility and color reactions similar to each other. For example, they are readily soluble in chloroform and methylene chloride, slightly soluble in benzene, ethanol, methanol and n-butanol and insoluble in water and n-hexane. Positive reactions with ferric chloride and Ehrlich reagents are obtained with negative reactions to Tollens, Sakaguchi and ninhydrin.

Characteristic physico-chemical properties of BBM-928 components of Example 3 are shown in Table 4.

TABLE 4

Physico-chemical Properties of BBM-928 Components A, B, C and D

| | BBM-928 | | | |
|---|---|---|---|---|
| | A | B | C | D |
| melting point | 246–248° C. | 214–217° C. | 244–248° C. | 224–227° C. |
| $[\alpha]_D^{25}$ (c 1, CHCl$_3$) | −27° | −74° | −91° | −13° |
| Anal. found C: | 53.19 | 50.14 | 51.77 | 50.75 |
| H: | 5.40 | 5.29 | 5.29 | 5.25 |

TABLE 4-continued

Physico-chemical Properties of
BBM-928 Components A, B, C and D

| | BBM-928 | | | |
|---|---|---|---|---|
| | A | B | C | D |
| N: | 12.92 | 12.34 | 13.55 | 12.58 |
| (by difference) O: | 28.49 | 32.23 | 29.39 | 31.42 |
| $\lambda_{max}$ in nm ($E_{1\ cm}^{1\%}$) | | | | |
| in EtOH | 235(586) | 235(570) | 235(638) | 235(550) |
| | 264(415) | 264(400) | 264(442) | 264(380) |
| | 345(165) | 345(163) | 345(173) | 345(155) |
| in EtOH—HCl | 234(610) | 234(556) | 234(650) | 234(565) |
| | 264(410) | 264(446) | 264(442) | 264(405) |
| | 345(165) | 349(188) | 345(173) | 345(165) |
| in EtOH—NaOH | 230(564) | 230(530) | 230(580) | 230(650) |
| | 256(763) | 256(775) | 256(704) | 256(930) |
| | 330(180) | 330(116) | 330(117) | 330(140) |
| | 383(170) | 383(122) | 383(122) | 383(145) |
| Mol. wt. (Osmometer, in CHCl₃) | 1,450 | — | 1,470 | — |

Figure 1:
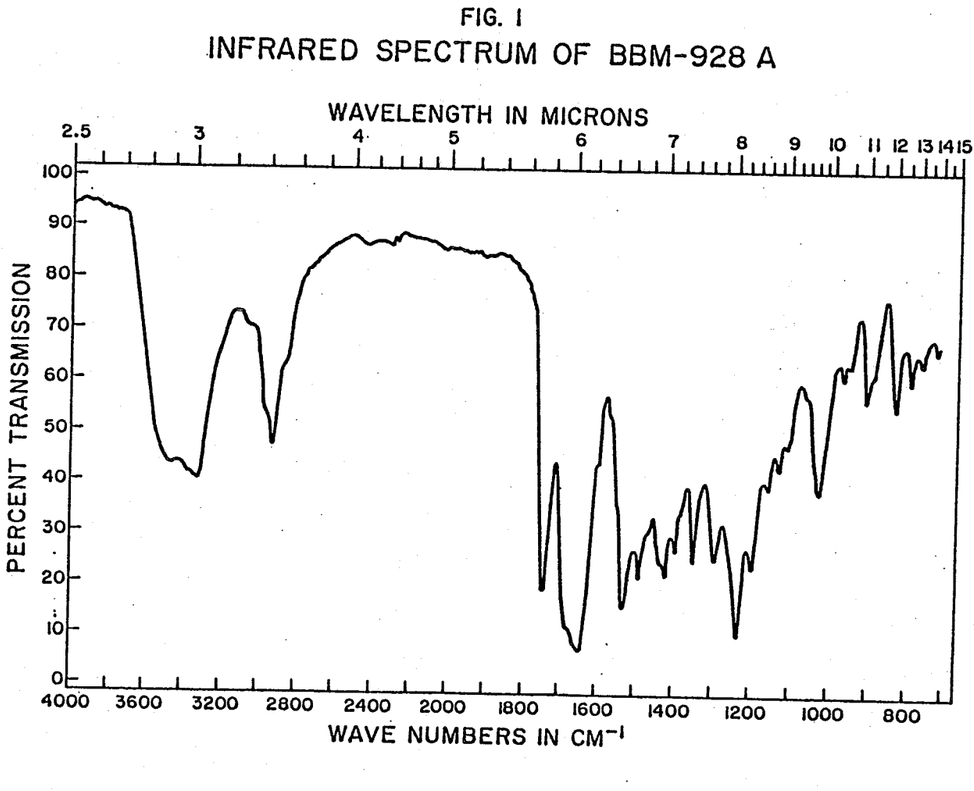
FIG. 1 is the infrared absorption spectrum of BBM-928A in potassium bromide.
Figure 2:
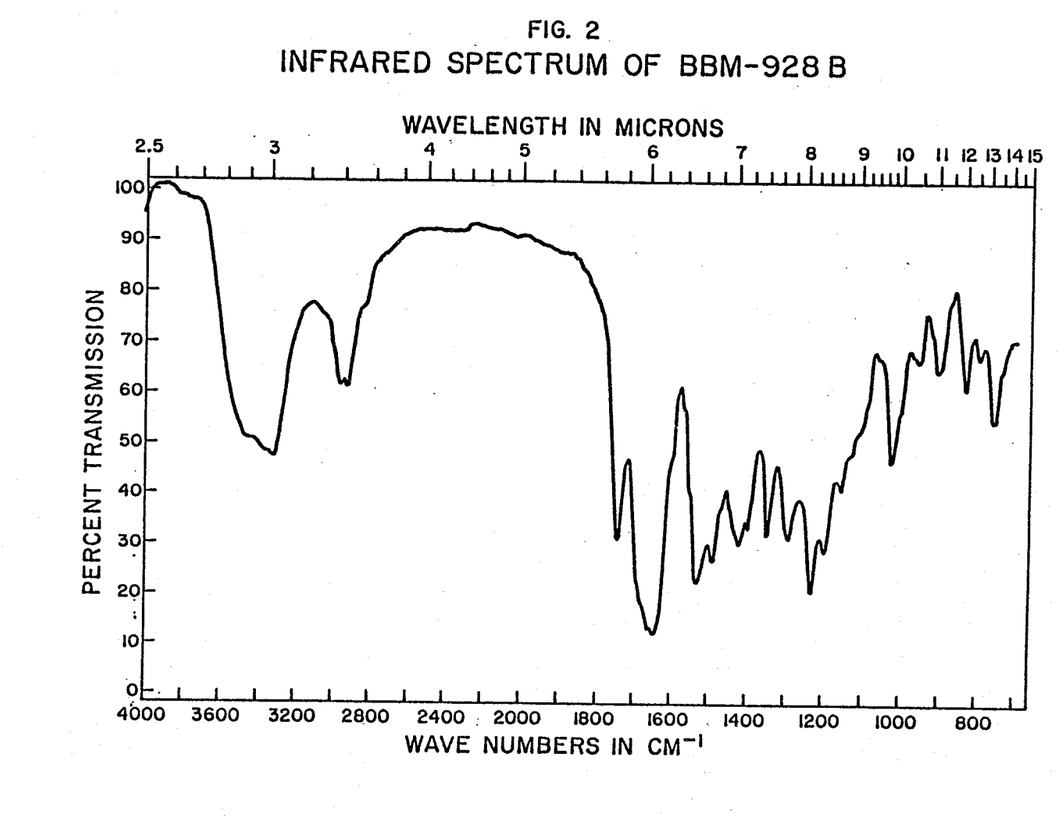
FIG. 2 is the infrared absorption spectrum of BBM-928B in potassium bromide.
Figure 3:
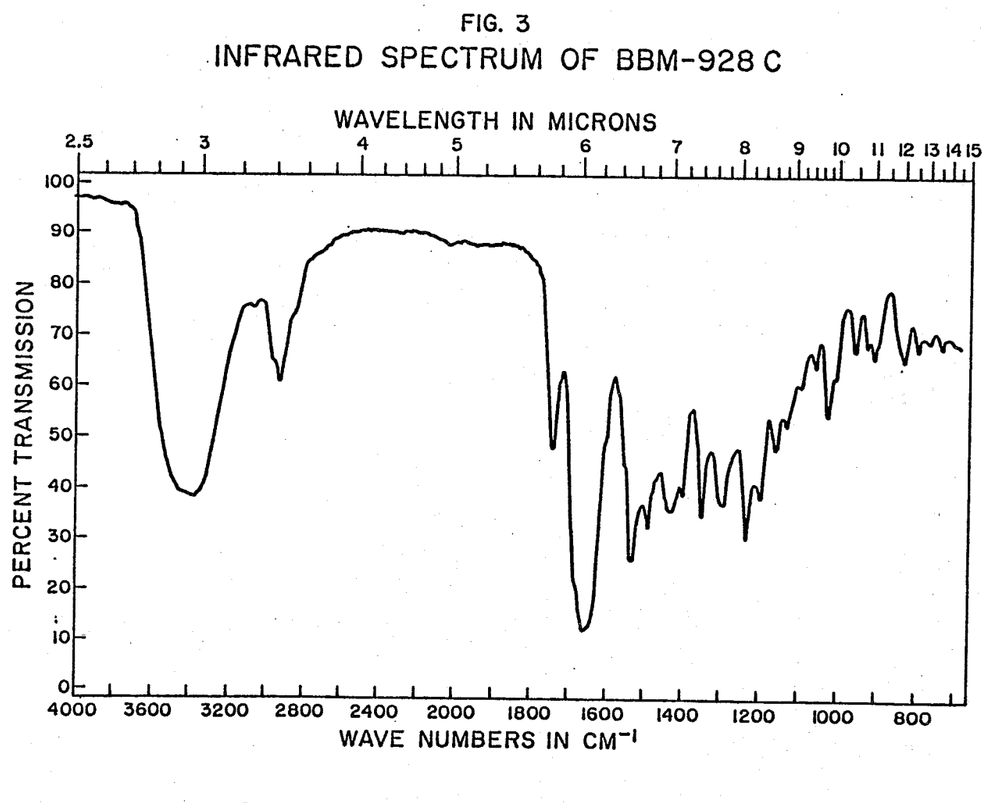
FIG. 3 is the infrared absorption spectrum of BBM-928C in potassium bromide.
Figure 4:
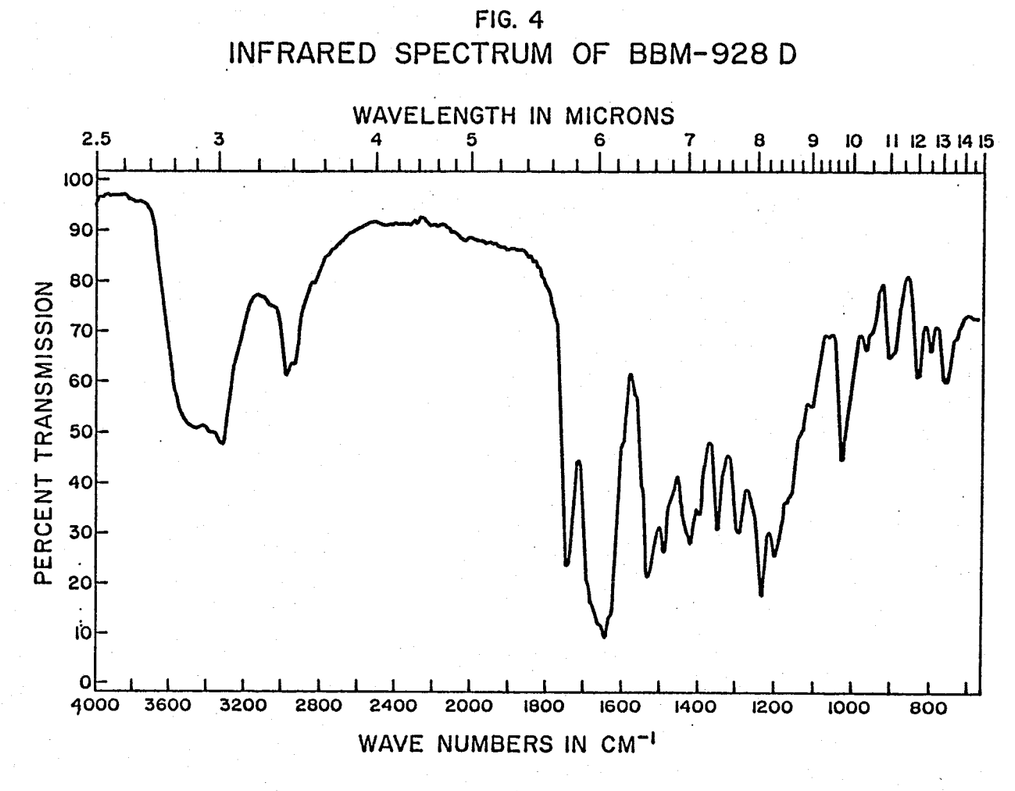
FIG. 4 is the infrared absorption spectrum of BBM-928D in potassium bromide.
Figure 5:
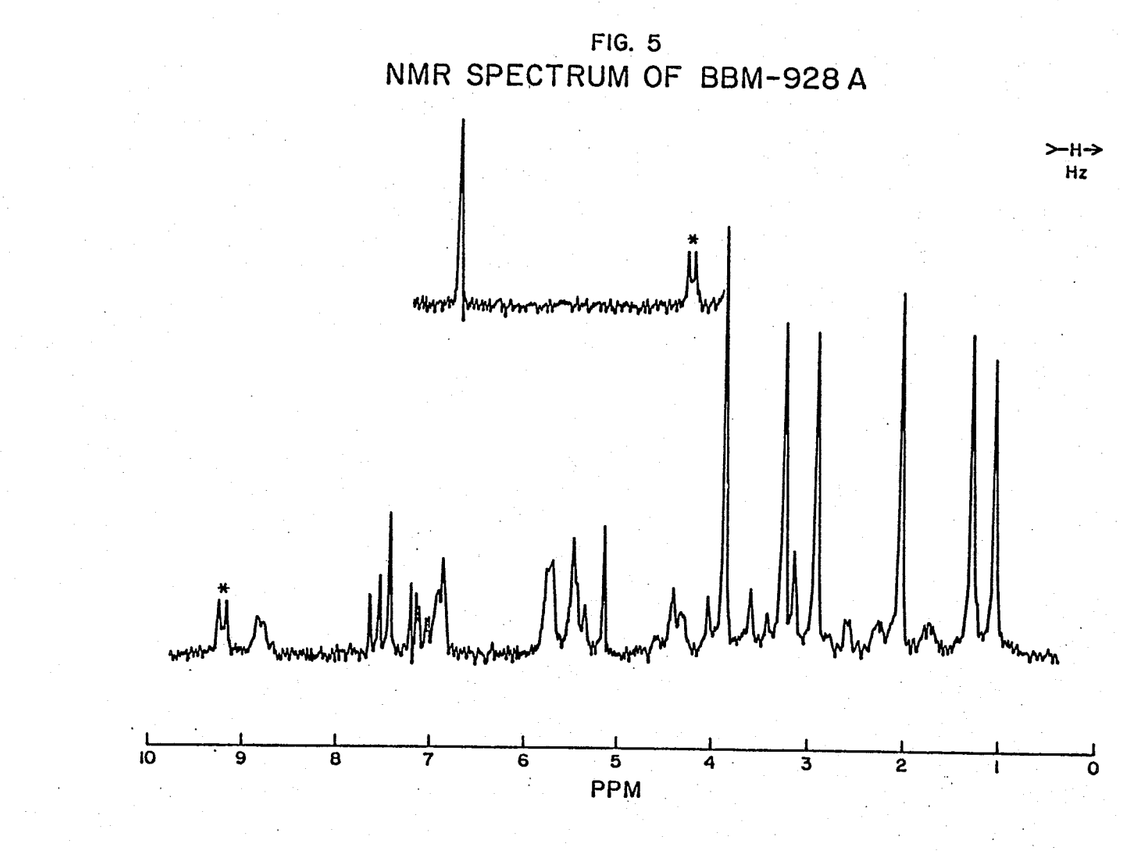
FIG. 5 shows the proton magnetic resonance spectrum of BBM-928A dissolved in deuterated chloroform using TMS as internal standard determined with a NMR spectrometer at a frequency of 90 MHz.
Figure 6:
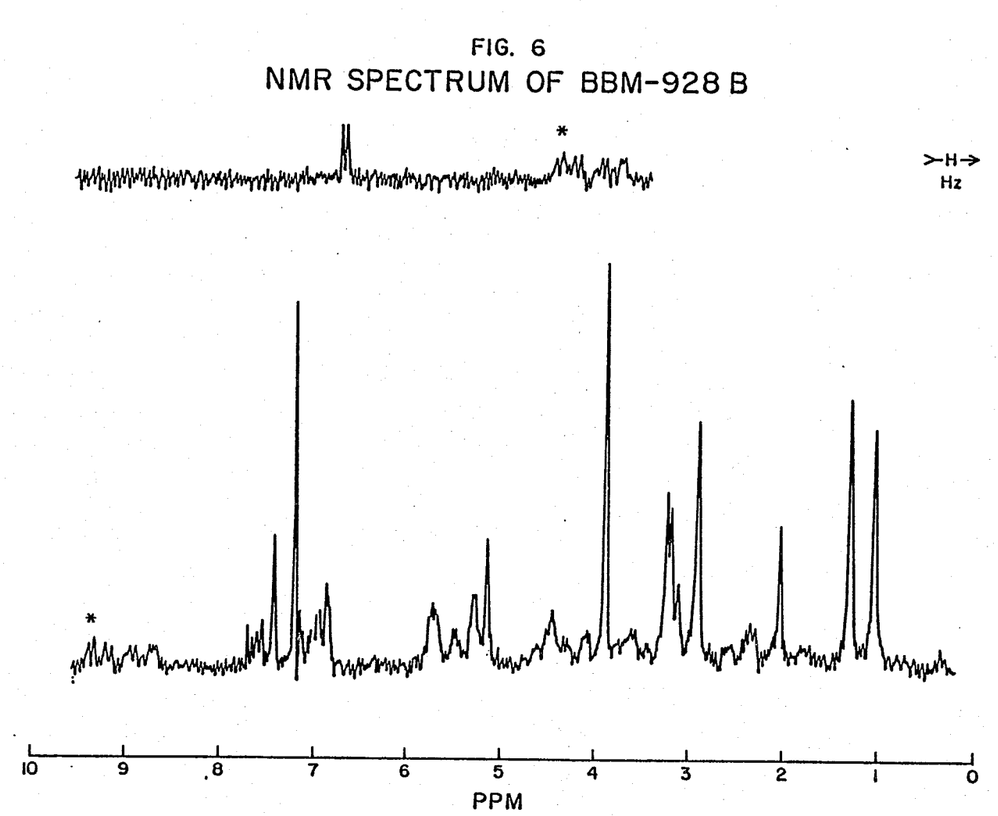
FIG. 6 shows the proton magnetic resonance spectrum of BBM-928B dissolved in deuterated chloroform using TMS as internal standard determined with a NMR spectrometer at a frequency of 90 MHz.
Figure 7:
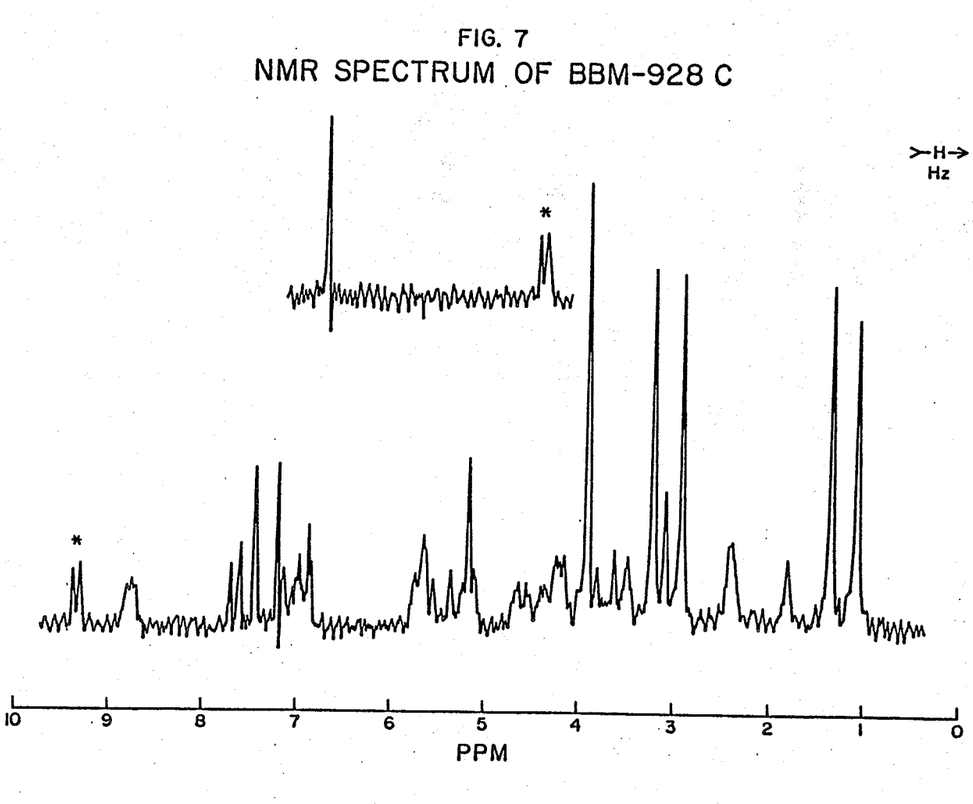
FIG. 7 shows the proton magnetic resonance spectrum of BBM-928C dissolved in deuterated chloroform using TMS as internal standard determined with a NMR spectrometer at a frequency of 90 MHz.
Figure 8:
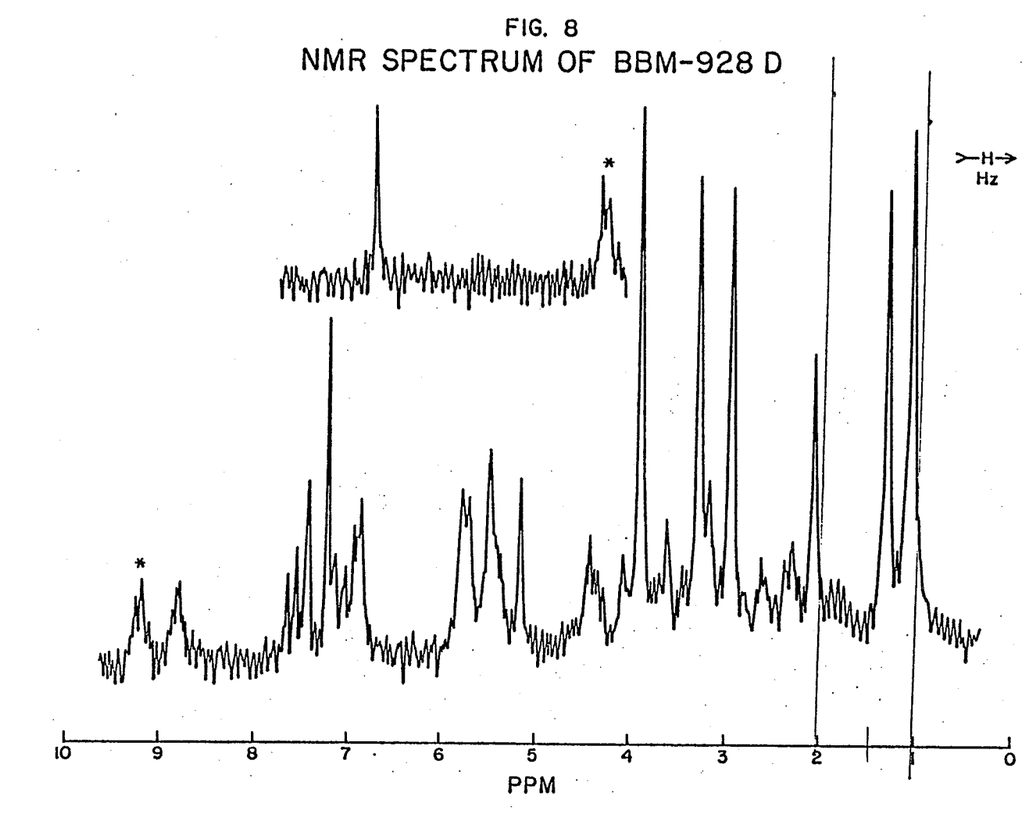
FIG. 8 shows the proton magnetic resonance spectrum of BBM-928D dissolved in deuterated chloroform using TMS as internal standard determined with a NMR spectrometer at a frequency of 90 MHz.

Infrared (IR) and nuclear magnetic resonance (NMR) spectra of components A, B, C and D are shown in FIGS. 1-4 and FIGS. 5-8, respectively, of the accompanying drawings. The NMR spectra of BBM-928A (FIG. 5), BBM-928B (FIG. 6), and BBM-928C (FIG. 7) are very similar to each other with the only difference being the presence of acetyl groups in components A ($\delta$: 2.03 ppm, 2 mol equivalent) and B ($\delta$: 2.05 ppm, 1 mol equivalent) but not in C. Upon acetylation with acetic anhydride in pyridine, 2, 3 and 4 molar equivalents of acetyl group were introduced to BBM-928 components A, B and C, respectively. The three acetylation products thus obtained showed identical properties in TLC, UV, IR and NMR spectra, indicating that BBM-928A is a monoacetyl derivative of BBM-928B and a diacetyl derivative of BBM-928C.

Acid hydrolysis of BBM-928A afforded five n-butanol-soluble, UV-absorbing fragments (I, II, III, IV and V) and five water-soluble, ninhydrin-positive substances (NPS-1, 2, 3, 4 and 5). The latter substances were separated by Dowex 50×4 chromatography and identified as the following amino acids:

| Compounds | Rf (S-123)* | Identification |
|---|---|---|
| NPS-1 | 0.72 | β-hydroxy-N—methylvaline (HM—Val) |
| NPS-2 | 0.49 | glycine (Gly) |
| NPS-3 | 0.46 | serine (Ser) |
| NPS-4 | 0.45 | sarcosine (sar) |
| NPS-5 | 0.23 | (Not assigned) |

*TLC, silica gel plate
S-123: 10% ammonium acetate - methanol - 10% ammonia solution (9:10:1)

The five UV-absorbing fragments referred to above are shown to have the following structures:

Fragment I
$C_{14}H_{14}N_2O_6$
MS: m/e 306 (M⁺)
$\lambda_{Max}^{MeOH}$: 227, 233, 251, 345 nm Fragment II
$C_{20}H_{25}N_3O_8$
MS: m/e 377 (M⁺-58)
$\lambda_{max}^{MeOH}$: 229, 234, 261, 345 nm Fragment III
$\lambda_{max}^{MeOH}$: 230, 235, 262, 345 nm Fragment IV
$C_{10}H_7NO_4$
MS: m/e 205 (M⁺)
$\lambda_{max}^{MeOH}$: 228, 260, 354 nm

Fragment V
$C_{23}H_{30}N_4O_9$
$\lambda_{max}^{MeOH}$: 230, 235, 262, 345 nm Upon acid hydrolysis (6N HCl), Fragments I, II, III and V gave the following degradation products:

| Fragment | Hydrolysis condition | |
|---|---|---|
| | sealed tube 110°, 20 hrs | refluxed 110° C. 3 hrs |
| I | IV, Ser | — |
| II | IV, Ser, HM—Val | I, HM—Val |
| III | IV | — |
| V | — | I, HM—Val, Sar |

Ser: serine
HM—Val: β-hydroxy-N—methylvaline
Sar: sarcosine

Base hydrolysis of BBM-928A or BBM-928C with 0.1N NaOH at 25° C. for 3 hr. provides Fragment VI (abbreviations Ser, HM-Val, and Sar are as stated above with Gly representing glycine and the symbol "X" representing an unassigned moiety)

Fragment VI

Treating Fragment VI with 0.1N HCl at 110° C. for 1 hr. provides Fragment VII plus HM-Val.

Fragment VII

Treating Fragment VI with 0.1N NaOH at 37° C. for 40 Hr. provides Fragment VIII plus Fragment I.

Fragment VIII

Treating Fragment VII with 0.1N NaOH at 37° C. for 40 hr. provides Fragment IX plus Fragment I.

X⟶Gly⟶Sar    Fragment IX

The unassigned moiety (X) has a molecular formula of $C_5H_6N_2O_2$ (in peptide form) based on microanalysis of Fragment IX and other peptide fragments containing (X) and spectral analysis summarized below.

| $^{13}C$—NMR | Proton-NMR | Assignment |
|---|---|---|
| 30.14 (t) | 2.36 ppm (2H, m) | —$CH_2$— |
| 61.4 (d) 61.7 (d) | 4.2–4.5 (2H, m) | 2 × —CH⟨ (O or N) |
| 140.7 (d) | 6.76 (1H, t) | —CH=N— |
| 171 (s) | — | —CO— (amide) —OH NH |

According to spectral data for Fragments VIII and IX and a 360 MHz proton NMR of BBM-928$A_p$ of Example 4, the unassigned amino acid moiety (X) appears to be best respresented by the following tetrahydropyridazine structure:

(X)

Based on the results of the above-described degradation experiments, spectral data, microanalysis and molecular weight determinations, the following structures are believed to best represent BBM-928A, B and C:

| | $R_1$ | $R_2$ | |
|---|---|---|---|
| BBM-928 A | Ac | Ac | Ser: serine |
| BBM-928 B | Ac | H | Gly: glycine |

| | R₁ | R₂ | |
|---|---|---|---|
| BBM-928 C | H | H | Sar: sarcosine |
| | | | HM—Val: β-hydroxy-N—methylvaline |

ANTIMICROBIAL ACTIVITY

Antimicrobial activity of BBM-928 components was determined against a variety of bacteria and fungi by serial agar dilution method in nutrient agar at pH 7 using Steer's multi-inoculating apparatus. The inoculum size was standardized to apply a 0.0025-ml aliquot of test organisms containing approximately $10^4$ cell/ml for all bacteria and fungi except acid-fast bacteria for which a $10^6$ cell/ml suspension was used. Minimum inhibitory concentrations (MIC), determined after overnight incubation at 37° C., are shown in Table 5. As seen therein, BBM-928 components are moderately to weakly active against gram-positive and acid fast bacteria but practically inactive against gram-negative bacteria and fungi.

The activity of prophage induction in lysogenic bacterium (ILB) was determined for BBM-928 components. No significant ILB activity was demonstrated with BBM-928 components A, B and C up to a concentration of 100 mcg./ml.

Lung (LL) carcinoma, and sarcoma 180 ascites (S180). Test solutions of the BBM-928 components in 0.9% saline containing 10% dimethylsulfoxide and mitomycin C in 0.9% saline were administered once a day according to dosing schedules ranging from a single one-day treatment to multiple daily treatments. By varying dosage, the minimum effective dose (MED) was determined which provided a median survival time value for the treated animals at least 1.25 times greater than a control group. This level of activity is considered to be a measure of significant antitumor activity. Results are shown in Table 6 along with calculated activity ratios illustrating that BBM-928A is markedly more active than mitomycin C by a factor of 10 to 300 depending upon the tumor strain and dosing schedule. Intraperitoneal $LD_{50}$ values of BBM-928 components A, B, C and D and mitomycin C determined by the method of Van der Waerden, Arch. Expt. Path. Pharmak., 195, 389 (1940), are also shown in Table 6.

TABLE 5

In Vitro antimicrobial Activity of BBM-928 Components Against Aerobic Bacteria

| BBRI Code | Test Organism | BBM-928 Components (MIC in mcg/ml) | | | | | |
|---|---|---|---|---|---|---|---|
| | | A | B | C | D | E | F |
| Sa-1 | S. aureus 209P | 12.5 | 25 | 50 | 100 | 100 | 25 |
| Sp-1 | S. pyogenes S-23 | 6.3 | 12.5 | 25 | 50 | 50 | 12.5 |
| Sl-1 | S. lutea PCI 1001 | 6.3 | 12.5 | 50 | 50 | 50 | 25 |
| Mf-1 | M. flavus D12 | 12.5 | 25 | 50 | 100 | 100 | 25 |
| Cr-1 | C. xerosis 53K-1 | 25 | 50 | >100 | >100 | >100 | 50 |
| Bs-1 | B. subtilis PCI 219 | 25 | 25 | 100 | 100 | 100 | 25 |
| Bg-1 | B. megaterium D2 | 25 | 25 | 50 | 100 | 100 | 25 |
| Ba-3 | B. anthracis A9504 | 6.3 | 12.5 | 25 | 50 | 50 | 12.5 |
| M6-1 | M. smegmatics 607 D87 | 25 | 25 | 25 | 100 | 100 | 25 |
| Mp-1 | M. phlei D88 | 12.5 | 12.5 | 12.5 | 50 | 50 | 12.5 |
| Ec-1 | E. coli NIHJ | >100 | >100 | >100 | >100 | >100 | >100 |
| Kp-1 | K. pneumoniae D-11 | >100 | >100 | >100 | >100 | >100 | >100 |
| Pa-3 | P. aeruginosa A9930 | >100 | >100 | >100 | >100 | >100 | >100 |
| Pv-1 | P. vulgaris A9436 | >100 | >100 | >100 | >100 | >100 | >100 |
| Pm-1 | P. mirabilis A9554 | >100 | >100 | >100 | >100 | >100 | >100 |
| Pg-1 | P. morganii A9553 | >100 | >100 | >100 | >100 | >100 | >100 |
| Sm-1 | S. marcescens A20019 | >100 | >100 | >100 | >100 | >100 | >100 |
| Al-1 | A. faecalis ATCC 8750 | >100 | >100 | >100 | >100 | >100 | >100 |
| Ca-1 | C. arbicans IAM 4888 | >100 | >100 | >100 | >100 | >100 | >100 |
| Cn-3 | C. neoformans | 100 | >100 | 100 | >100 | >100 | >100 |

ANTITUMOR ACTIVITY

Comparative testing of BBM-928 components A, B, C and D with mitomycin C for antitumor activity was carried out with the intraperitoneally implanted tumors: P388 leukemia, L1210 leukemia, B16 melanoma, Lewis

TABLE 6

Antitumor Activity and Toxicity of

| Minimum Effective Dose (MED, mg/kg/day) | | | | | $LD_{50}$, i.p. |
|---|---|---|---|---|---|
| P388 | L1210 | B16 | LL | S180 | (mg/kg/day) |

TABLE 6-continued

| | Minimum Effective Dose (MED, mg/kg/day) | | | | LD$_{50}$, i.p. (mg/kg/day) |
|---|---|---|---|---|---|
| | P388 | L1210 | B16 | LL | S180 | |
| BBM-928 A, B, C, and D and Mitomycin C | | | | | | |
| Treatment[a] | | | | | | |
| BBM-928A | 0.003 | >0.1 | 0.003 | 0.03 | 0.003 | 0.13 |
| BBM-928B | 0.1 | — | — | — | — | 0.18 |
| BBM-928C | — | — | — | — | — | 0.81 |
| BBM-928D | 0.003 | — | — | — | — | 0.083 |
| Mitomycin C | 0.1 | 3 | 1 | 0.3 | 0.3 | 9.3 |
| Treatment[b] | | | | | | |
| BBM-928A | 0.001 | 0.003 | 0.003 | 0.003 | 0.0001 | 0.013 |
| Mitomycin C | 0.1 | 0.3 | 0.3 | 0.3 | 0.03 | 1.4 |
| Activity Ratio (BBM-928A vs. Mitomycin C) | | | | | | |
| Treatment[a] | 30 | — | 300 | 10 | 100 | |
| Treatment[b] | 100 | 100 | 100 | 100 | 100 | |

[a]single treatment on day 1.
[b]daily treatments from day 1 to day 9.

EXAMPLE 1

Production of BBM-928 Complex

Agar Fermentation: A well-grown agar slant of a strain of Actinomycetes species G455-101 is used to inoculate vegetative medium containing 2% soluble starch, 1% glucose, 0.5% Pharmamedia, 0.5% yeast extract, 0.5% NZ-amine (Type A) and 0.1% CaCO$_3$ with the pH being adjusted to 7.2 before sterilization. The seed culture is incubated at 32° C. for 72 hours on a rotary shaker (250 rpm), and 5 ml. of the growth is transferred to a 500 ml. Erlenmeyer flask containing 100 ml. of fermentation medium composed of 2% soluble starch, 1% Pharmamedia, 0.003% ZnSO$_4$.7H$_2$O and 0.4% CaCO$_3$. The production of the BBM-928 complex generally reaches maximum after about 5 days shaking culture.

Tank Fermentation: A seed culture is shaken for 4 days in Erlenmeyer flasks and inoculated to 100 liters of germination medium composed of 2.0% oat meal (Quaker Products, Australia), 0.5% glucose, 0.2% dry yeast, 0.0008% MnCl$_2$.4H$_2$O, 0.0007% CuSO$_4$.7H$_2$O, 0.0002% ZnSO$_4$.7H$_2$O and 0.0001% FeSO$_4$.7H$_2$O in a 200 liter seed tank fermentor which is stirred at 200 rpm. at 30° C. for 54 hours. A 15-liter portion of the seed culture is then inoculated to 170 liters of fermentation medium containing 2.0% soluble starch, 1.0% Pharmamedia, 0.0003% ZnSO$_4$.7H$_2$O and 0.4% CaCO$_3$ in a 400-liter tank fermentor which is operated at 30° C. at 200 rpm with an aeration rate of 150 liters/min. The broth pH gradually increases with the progress of fermentation and reaches 8.4–8.5 after 100–120 hours at which time a peak antibiotic potency of 30 mcg/ml is obtained.

EXAMPLE 2

Isolation of BBM-928 Complex by Solvent Extraction

Harvested broth (170 liters, pH 8.5) from Example 1 is filtered with a clarifying agent. Activity is found in both the mycerial cake and filtrate. The mycerial cake is extracted twice with a solvent mixture of acetone and methanol (1:1, 30 liter×2). Extracts are combined and evaporated under reduced pressure to give an aqueous concentrate which is extracted with n-butanol. The broth filtrate is extracted twice with n-butanol (40 liter×2). Concentration of the combined-n-butanol extracts under reduced pressure and lyophylization of the residue provides a crude solid (21.4 g.). According to thin layer chromatography assay, this material is a complex consisting of three major components, A, B and C, and three minor components, D, E and F having Rf values as set forth in Table 7 below.

TABLE 7

| Silica gel TLC of BBM-928 Components | | |
|---|---|---|
| | Rf Values* | |
| | System N-118** | System N-103*** |
| BBM-928A | 0.71 | 0.48 |
| BBM-928B | 0.53 | 0.26 |
| BBM-928C | 0.27 | 0.07 |
| BBM-928D | 0.73 | 0.53 |
| BBM-928E | 0.56 | 0.34 |
| BBM-928F | 0.39 | 0.17 |

*detection by UV scanner (Shimadzu CS-910) at 345 nm
**n-butanol - methanol - water (63:27:10)
***xylene - methylethylketone - methanol (5:5:1)

EXAMPLE 3

Purification of BBM-928 Complex

The crude complex of Example 2 is purified by a preparative counter current distribution apparatus (Mitamura, 100 ml/tube) using a solvent system of carbon tetrachlorode-chloroform-methanol-water (5:2:5:1). After 50 transfers, tube Nos. 5 through 20 are combined and concentrated to give pale yellow powder (4.4 g.) containing components A, B, D, E and F. This mixture is dissolved in a small amount of chloroform and charged on a column of silica gel C-200 (500 ml.) which is pretreated with ethyl acetate. The column is developed by ethyl acetate with an increasing amount of methanol (2–5%, V/V) and fractions monitored by optical density at 345 nm. Minor component D is eluted first with ethyl acetate followed by component A. Components E, B and F are eluted next in that order at 3% methanol concentration. Each fraction containing the appropriate component is evaporated under reduced pressure and the residue crystallized from chloroform-methanol. Likewise, crude preparation of component C is obtained from tube Nos. 21 through 35 of the above-described counter current distribution. Purification of component C is carried out by silica gel chromatography and crystallization from chloroform-methanol. Yields for components A, B, C, D, E and F are, respectively, 988 mg., 420 mg., 848 mg., 130 mg., 119 mg., and 114 mg.

EXAMPLE 4

Further Purification of Component BBM-928A of Example 3

Thin layer chromatography assay of the BBM-928A component of Example 3 (employing a system consisting of 10% methanol in toluene) indicated the sample was not completely homogenous in that it contained additional material running just ahead of the BBM-928A component. The following steps were carried out to effect purification.

(1) The sample is chromatographed on silica gel using a linear gradient of chloroform to 6% methanol-chloroform. Fractions eluting between 2.4 and 3.3% methanol-chloroform (containing the BBM-928A component plus some container) are composited for the next step.

(2) A concave gradient is generated using three vessels containing 2% methanol toluene in the first two and 6% methanol-toluene in the third. The composite from Step 1 chromatographed (silica gel column) on this gradient provides a minor component which elutes first closely followed by the purified BBM-928A component (referred to herein as BBM-928A$_p$).

Molecular weight of BBM-928A$_p$, as determined by Field Desorption Mass Spectrometry, is 1427 corresponding to an empirical formula of $C_{64}H_{78}N_{14}O_{24}$ (MW 1427.417).

Elemental Analysis (Samples dried at 100° C. for 18 hours).

|  | C | H | N | O[a] |
|---|---|---|---|---|
| Calculated for $C_{64}H_{78}N_{14}O_{24}$ | 53.85 | 5.51 | 13.74 | 26.90 |
| Found[b] | 52.47 | 5.48 | 13.81 | 28.24[a] |

[a]By difference.
[b]Average of three determinations.

The physico-chemical properties of BBM-928D relative to those of BBM-928A, B, and C are summarized in Tables 4 and 7. They are similar but with differences in melting point, specific rotation, and Rf value in the N-118 and N-103 solvent systems indentified in Table 7. The general spectral patterns of all four substances are very similar signifying similar structures, but with certain notable differences in the NMR spectra.

The NMR spectrum of BBM-928D (FIG. 8) differs from that of BBM-928A (FIG. 5) only in the presence of one acetyl (δ: 2.06 ppm, s) and one propionyl (δ: 1.06, t and 2.33 ppm, q) group in BBM-928D and two acetyl signals (δ: 2.06 ppm, s) in BBM-928A.

Complete acid hydrolysis of BBM-928D (6N HCl, 100° C., 18 hrs.) in the fashion indicated above for BBM-928A afforded the same five hydrolysis products in equimolar ratio as were afforded by BBM-928A, viz. 3-hydroxy-6-methoxy-quinaldic acid and the four amino acids glycine, sarcosine, D-serine, and L-β-hydroxy-N-methylvaline. The structural difference between BBM-928A and BBM-928D is therefore in amino acid moiety X referred to above, (3S,4S)-4-hydroxy-2,3,4,5-tetrahydropyridazine-3-carboxylic acid, which is present as the acetate ester in BBM-928A.

Upon mild alkaline hydrolysis (0.01N $Na_2CO_3$, 25° C., 30 min.) BBM-928D afforded BBM-928C, the non acylated family member. Thus, BBM-928D is the monoacetyl-monopropionyl derivative of BBM-928C, that is the general formula given above for BBM-928A, B, and C wherein for BBM-928D $R_1$ is acetyl and $R_2$ is propionyl; molecular formula $C_{65}H_{80}N_{14}O_{24}$ differing from that of BBM-928A by one $CH_2$-unit.

We claim:

1. The pharmaceutical antitumor antibiotic composition in sterile injectible form comprising a pharmaceutical carrier substance, and BBM-928A having the formula

2. The pharmaceutical antitumor antibiotic composition in sterile injectible form comprising a pharmaceutical carrier substance, and BBM-928B having the formula 3. The pharmaceutical antitumor antibiotic composition in sterile injectible form comprising a pharmaceutical carrier substance, and BBM-928C having the formula 4. The pharmaceutical antitumor antibiotic composition in sterile injectible form comprising a pharmaceutical carrier substance, and BBM-928D having the formula

* * * * *